United States Patent
Heine et al.

(10) Patent No.: US 9,089,296 B2
(45) Date of Patent: Jul. 28, 2015

(54) ILLUMINATION DEVICE AND BOTTOM UNIT, ESPECIALLY FOR MEDICAL DIAGNOSTIC INSTRUMENTS

(75) Inventors: Oliver Heine, Herrsching (DE); Dirk Schade, Penzberg (DE); Ralf Schneider, Munich (DE); Elsa Ploetz, Andechs (DE); Anton Schneider, Gilching (DE); Bela Michael Rohrbacher, Heidenheim (DE); Markus Atzenbeck, Landsberg am Lech (DE)

(73) Assignee: Heine Optotechnik GmbH & Co KG, Herrsching (DE)

( * ) Notice: Subject to any disclaimer, the term of this patent is extended or adjusted under 35 U.S.C. 154(b) by 1302 days.

(21) Appl. No.: 12/939,670

(22) Filed: Nov. 4, 2010

(65) Prior Publication Data
US 2011/0112378 A1 May 12, 2011

(30) Foreign Application Priority Data

Nov. 9, 2009 (DE) .......................... 10 2009 052 380
Mar. 24, 2010 (DE) .......................... 20 2010 004 123

(51) Int. Cl.
*A61B 1/06* (2006.01)
*A61B 1/267* (2006.01)
(Continued)

(52) U.S. Cl.
CPC ............. *A61B 1/267* (2013.01); *A61B 1/00034* (2013.01); *A61B 1/0684* (2013.01); *A61B 1/00032* (2013.01); *A61B 2018/1226* (2013.01); *A61B 2560/0431* (2013.01)

(58) Field of Classification Search
CPC .................................................... A61B 1/0684
See application file for complete search history.

(56) References Cited

U.S. PATENT DOCUMENTS

| 4,147,163 | A | 4/1979 | Newman et al. |
| 4,382,219 | A | 5/1983 | Heine et al. |
| 5,153,495 | A | 10/1992 | Connors |

(Continued)

FOREIGN PATENT DOCUMENTS

| DE | 2852956 | 6/1980 |
| DE | 10161017 A1 | 6/2003 |

(Continued)

OTHER PUBLICATIONS

Official action dated Mar. 3, 2011 for EP 10 19 0304.

*Primary Examiner* — Andrew Yang
(74) *Attorney, Agent, or Firm* — Bachman & LaPointe, P.C.

(57) ABSTRACT

An illumination device comprises at least one LED (36), which can be connected through circuit means (50) to a voltage source optionally formed by a battery unit (70) or an accumulator unit (74). Furthermore, a first contact means (60) is provided for connecting the battery unit (70) and a second contact means (64) for connecting the accumulator unit (74) to the circuit means (50). A bottom unit for a battery grip (11) comprising a grip sleeve (90) in which the accumulator unit (74) is arranged, has a basic body (84) mountable at the lower end of the grip sleeve (90), wherein an upper contact element (89) for contacting the accumulator unit (74) and a lower contact element (95) for contacting a contact element (107) of a charging station, to which a current is applied, are arranged in the basic body (84). An electronic circuit unit (99) having a microprocessor (1) is connected between the upper and the lower contact elements (89, 95), which electronic circuit unit (99) is formed and configured such that it controls a charging process for charging the accumulator unit (74).

24 Claims, 6 Drawing Sheets

(51) Int. Cl.
*A61B 1/00* (2006.01)
*A61B 18/12* (2006.01)

(56) References Cited

U.S. PATENT DOCUMENTS

| | | |
|---|---|---|
| 5,542,904 A | 8/1996 | Heine et al. |
| 6,130,520 A | 10/2000 | Wawro et al. |
| 6,391,490 B1 | 5/2002 | Aoi et al. |
| 2004/0183482 A1 | 9/2004 | Roberts et al. |
| 2006/0247497 A1 | 11/2006 | Gardner |
| 2007/0255108 A1 | 11/2007 | Schmitz |
| 2008/0228038 A1 * | 9/2008 | McMahon et al. ............ 600/223 |
| 2009/0267541 A1 | 10/2009 | Hsu |
| 2010/0022843 A1 | 1/2010 | Pecherer et al. |

FOREIGN PATENT DOCUMENTS

| | | |
|---|---|---|
| DE | 20308431 U1 | 7/2003 |
| DE | 69922166 T2 | 5/2005 |
| WO | 2008111057 | 9/2008 |

* cited by examiner

ILLUMINATION DEVICE AND BOTTOM UNIT, ESPECIALLY FOR MEDICAL DIAGNOSTIC INSTRUMENTS

CROSS-REFERENCE TO RELATED APPLICATION

This application claims benefit of German Patent Application 10 2009 052 380.4, filed Nov. 9, 2009, and German Utility Model Application 20 2010 004 123.6, filed Mar. 24, 2010, the disclosures of which are incorporated herein in its entirety by reference.

BACKGROUND OF THE INVENTION

1. Field of the Invention

The invention relates to an illumination device having at least one LED which can be connected through circuit means to a voltage source, which is selectively formed by a battery unit or an accumulator unit, as well as an intelligent bottom unit for controlling the charge of the accumulator unit. The illumination device and the bottom unit are particularly suitable for handgrips of medical diagnostic instruments, such as a laryngoscope.

2. Description of the Background Art

DE 203 08 431 U1 discloses a handgrip for a laryngoscope having a cylindrical elongate housing made of plastics into which a light insert is inserted, which light insert has an elongate battery body of cylindrical shape. A light bulb is provided at the top side of the battery body, which light bulb protrudes into an insertion piece made of transparent material at the upper end of the housing. The light bulb is upwardly biased through biasing means and is slidable in the longitudinal direction of the battery body. A battery unit consisting of two dry batteries having 1.5 V each can be inserted in the battery body, resulting in a voltage of 3 V altogether. It is also possible to introduce an accumulator unit in the battery body, wherein the voltage of a newly charged accumulator usually amounts to 4 V.

Due to technological reasons there are limits to the brightness, i.e. the luminous flux and the illumination intensity, of the light bulbs used in the prior art. The service life of a light bulb in most cases amounts to a few hours.

A possible alternative to the light bulb is nowadays increasingly offered by the LED (light emitting diode) technology. The values for luminous flux and illumination intensity of LEDs can considerably exceed the values of light bulbs. Moreover, the service life to be expected for an LED is multiple times as high as the one of a light bulb.

In the case of LED applications presently used in most cases pre-resistors connected in series are inserted in addition to the LED and then connected to a voltage source (battery or accumulator). The brightness of the LED is thus dependent on the voltage of the battery or the accumulator and therefore fluctuates in an undesirable manner.

The LED should in principle be supplied with a constant current in order to guarantee a uniform brightness irrespective of the battery voltage. In this regard, it is conceivable to supply the LED through a current regulator with a constant current irrespective of the voltage applied.

If, however, it is desired to give a user the possibility to choose between dry batteries and accumulators, the problem arises that different ranges of operation are to be observed for the different types of voltage sources. A dry battery supplies an electronic system with fundamentally different input voltage values than, for example, a Li-ion accumulator cell.

Normally in the case of laryngoscopes two dry batteries connected in series or an accumulator cell are used as energy supply. The two dry batteries connected in series have a range of operation of 2 to 3 V, whereas the accumulators have an operating range of 3 to 4 V.

It is not possible to operate a current regulator in a universal operating range from 2 to 4 V, because this would lead to damage of the accumulators. In order to protect the accumulators, it is indispensable to operate them only up to approximately 3 V. Operating them with a voltage of 2V would lead to irreversible damage of the accumulators.

Known diagnostic instruments operated with accumulator units do neither give an indication of the charging state of the accumulator unit nor do they have any charging management to optimize the charging process. Thus the charging time is not optimized, and furthermore the user does not know whether and if so, for how long he/she can still use the diagnostic instrument until the accumulator unit has to be recharged. This is the more problematic, the older, and thus the more unreliable, an accumulator unit is.

SUMMARY OF THE INVENTION

The object underlying the invention is to create an illumination device having at least one LED guaranteeing a uniform brightness of the LED irrespective of the battery voltage without endangering the functionability of the battery unit or the accumulator unit. Another object is to create a bottom unit for the handgrip of a diagnostic instrument guaranteeing optimal charging of the accumulator unit.

According to a first aspect of the invention the illumination device comprises at least one LED which can be connected through circuit means selectively with a battery unit or an accumulator unit, wherein two different contact means are provided for connecting the battery unit and the accumulator unit, respectively, to the circuit means. The battery unit and the accumulator unit are mutually interchangeable. Depending on the fact to which contact means a voltage is applied, the circuit means is able to recognize whether a battery unit or an accumulator unit is used.

In the case of a preferred embodiment the circuit means comprises an electronic circuit unit connected to the first contact means and to the second contact means as well as to the LED. The electronic circuit unit is formed and configured such that it performs a first operating mode if the first contact means is connected to the battery unit, and performs a second operating mode if the second contact means is connected to the accumulator unit. Due to the fact that the electronic circuit unit is able to perform two different operating modes, it is possible to perform one operating mode such that it is adapted to the battery unit and the other operating mode such that it is optimal for the accumulator unit.

Preferably, in this embodiment, the electronic circuit unit is formed and configured such that in a first operating mode it applies a first power to the LED if the battery voltage exceeds a first battery threshold, and no power to the LED if the battery voltage falls below the first battery threshold by a certain extent.

In this way it is enabled that a constant power is applied to the LED if a battery unit is used and that the LED is turned off in case the battery voltage goes below the first battery threshold by the certain extent. This prevents the battery unit from being damaged. The certain extent may also be 0. In this case the LED is turned off if the battery voltage goes below the first battery threshold.

In an advantageous further development of this embodiment the electronic circuit unit is formed and configured such that in a first operating mode it applies a second constant power which is lower than the first power to the LED if the battery voltage goes below the first battery threshold and is higher than a second battery threshold. In this way, it is enabled that the user can recognize from the fact that the light of the LED becomes darker that the LED will be turned off soon.

Advantageously the first battery threshold amounts to 2.2 V to 2.6 V, preferably 2.4 V, and the second battery threshold 1.8 V to 2.2 V, preferably 2 V, if the battery unit comprises two dry batteries having a nominal voltage of 1.5 V each and being connected in series.

In the case of a further preferred embodiment the electronic circuit unit can be formed and configured such that in the second operating mode it applies a first power to the LED if the accumulator voltage exceeds a first accumulator threshold, and it applies no power to the LED if the accumulator voltage goes below the first accumulator threshold by a certain extent. By turning off the LED after the accumulator voltage has gone below the first accumulator threshold by the predetermined extent it is ensured that the accumulator voltage does not drop to such an extent that the accumulator unit is damaged. If the accumulator voltage lies above the first accumulator threshold, the LED is operated with a constant power. In this case, too, the certain extent may be O.

As in the case of the first operating mode, in the case of the second operating mode, too, a second power which is lower than the first power can be applied to the LED if the accumulator voltage goes below the first accumulator threshold and is higher than a second accumulator threshold which is lower than the first accumulator threshold, so that the user can recognize from the fact that the LED light becomes darker that the accumulator unit will have to be recharged soon, wherein the lower brightness in the case of operation with the second power is constant.

In the second operating mode the first accumulator threshold preferably amounts to 3.2 V to 3.6 V, preferably 3.4 V, and the second accumulator threshold 2.8 V to 3.2 V, preferably 3.0 V if the fully charged accumulator unit has a voltage of approx. 4 V.

Appropriately, the first and the second contact means are connected through an ON/OFF switch to the electronic circuit unit in order to interrupt the voltage supply between the battery unit or the accumulator unit to the electronic circuit unit if no illumination is required.

In order to adjust the brightness of the LED, a potentiometer can be provided by which the first power can be adjusted.

In order to charge the accumulator unit, a bottom unit according to the invention is used having a basic body mountable at the lower end of the grip sleeve of a handgrip, wherein an upper contact element for contacting the accumulator unit and a lower contact element for contacting a contact element of a charging station, to which a current is applied, are arranged in the basic body. An charging electronic circuit unit having a microprocessor is connected between the upper and the lower contact element, which charging electronic circuit unit is formed and configured such that it controls a charging process for charging the accumulator unit.

The charging electronic circuit unit preferably comprises charging state measuring means configured such that it measures the momentary charging state of an accumulator unit and forwards a corresponding signal to the microprocessor. A table is stored in the microprocessor for optimizing the charging time depending on the momentary charging state of the accumulator unit. The microprocessor is formed and configured such that it controls a charge regulator for regulating the charge of the accumulator unit corresponding to the table stored.

Preferably, a charging state display comprising one or more LEDs is provided at the bottom side of the bottom unit. The charging electronic circuit unit is formed and configured such that it displays the charging state of the accumulator unit through the charging state display, wherein it preferably turns off the charging state display when the lower contact element comes into contact with the contact element of the charging station and/or turns on the charging state display if the contact of the lower contact element with the contact element of the charging station is interrupted. In order to reduce the current consumption, the charging state display is preferably turned off again after a predetermined period of time has expired after it has been turned on.

In order to prevent that a consumer load that has been turned on consumes more current than can be charged, the charging electronic circuit unit appropriately comprises a switch in a conductor path connectable to the consumer load, and the microprocessor is formed and configured such that it opens the switch when the lower contact element comes into contact with the contact element of the charging station. The switch is closed again if the contact between the lower contact element and the contact element of the charging station is interrupted.

The illumination device according to the invention and the bottom unit according to the invention are preferably suitable for mounting in a laryngoscope handgrip. It is also conceivable to use them in other medical diagnostic instruments requiring illumination, such as otoscopes, dermatoscopes, ophthalmoscopes or else in hand lamps or pocket lamps.

BRIEF DESCRIPTION OF THE DRAWINGS

An embodiment of the invention will be explained hereinafter in more detail with reference to the accompanying drawings, in which.

DETAILED DESCRIPTION OF THE INVENTION

Figure 1:
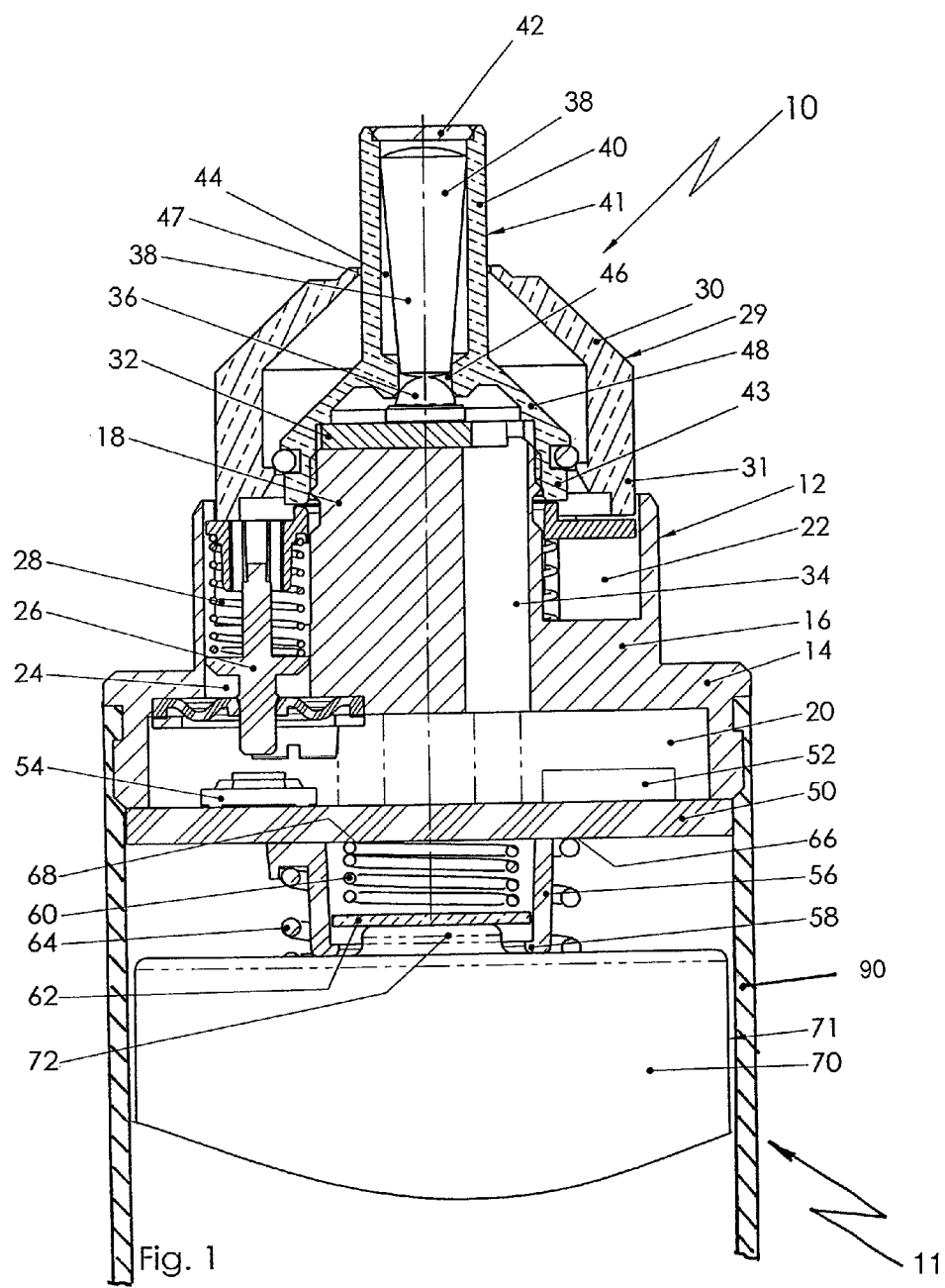
FIG. 1 is a longitudinal cross section of a battery grip for a laryngoscope in the area of an illumination device, wherein a dry battery unit is used as a voltage source.
Figure 2:
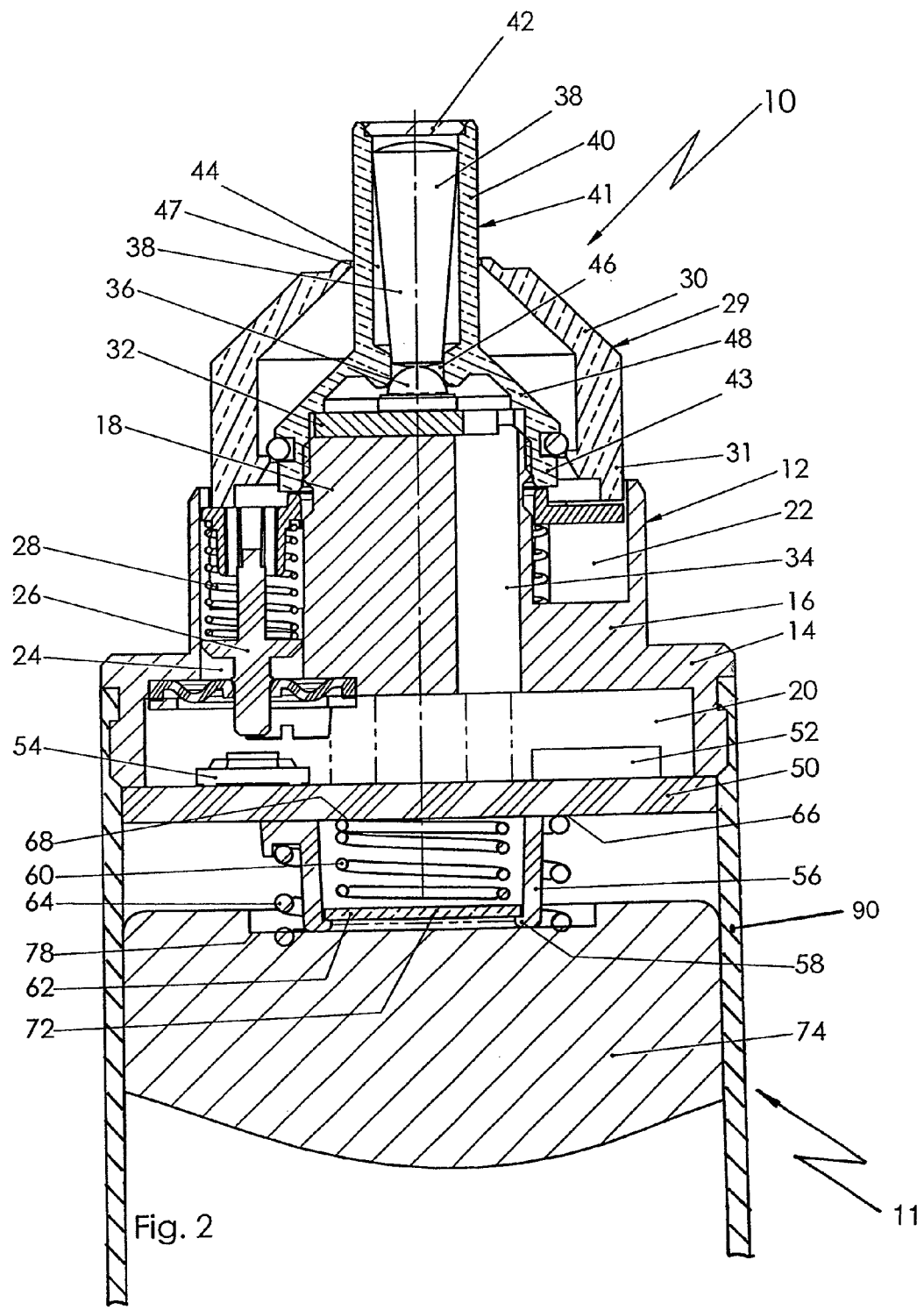
FIG. 2 shows the view of FIG. 1, wherein an accumulator unit is used as a voltage source.

The illumination device 10 shown in FIGS. 1 and 2 is inserted in a battery grip 11 of a laryngoscope. The illumination device 10 comprises a rotationally symmetrical basic body 12, the outer diameter of which decreases upwardly in a step-like manner, whereby a lower portion 14 is formed, the outer diameter of which is the largest and which is inserted in the upper end of a grip sleeve 90 of the battery grip 11. This lower portion 14 is followed by a middle portion 16, which is followed by an upper portion 18 having the smallest diameter. An illumination head 41 is placed above the upper portion 18, wherein the illumination head 41 comprises a lowermost cylindrical portion 43 surrounding the upper portion 18 of the basis body 12. The cylindrical portion 43 is followed by an upwardly tapering portion 48 in the shape of a truncated cone, which changes into an upper cylindrical portion 40, in which a cylindrical inner space 44 is formed which is concentric with respect to the longitudinal axis of the illumination device 10. The upper end of the cylindrical inner space 44 is closed by a transparent cover 42. A concentric through-hole 46 is formed at the lower end of the cylindrical portion 40, the diameter of the concentric through-hole 46 being smaller than the diameter of the cylindrical inner space 44. The upper part of an LED extends into the through-hole 46, followed by an optical system 38 extending in the direction of the transparent cover 42. The LED 36 is mounted centrally on a circuit board 32 mounted on the upper end face of the uppermost portion 18 of the basic body 12.

A cylindrical recess 20 is formed at the bottom side of the lower portion 14 of the basic body 12, which recess 20 is covered by a circuit board 50. An electronic circuit unit 52 is mounted on the circuit board 50. Furthermore, a micro-switch 54 is provided which can be actuated by a switch plunger 26 which is arranged slidably in parallel to the longitudinal axis of the illumination device 10 against the force of a helical spring 28 in an annular recess 22 formed in the top side of the middle portion 16 of the basic body 12 and which extends downwardly through a through-hole 24 on the left side in FIG. 1, wherein the through-hole 24 connects the recess 20 with the annular recess 22.

The illumination head 41 is surrounded by a pressure sleeve 29 slidable in the longitudinal direction of the illumination device 10, wherein the lower end of the pressure sleeve 29 is arranged in the annular recess 22 and the switch plunger 26 can be actuated by the pressure sleeve 29. The cylindrical portion 31 is followed by an upwardly tapering portion 30 in the shape of a truncated cone having in its upper end a through-hole 47 surrounding the cylindrical portion 40 of the illumination head 41 at half height.

A sleeve 56 made of insulating material is mounted concentrically at the bottom side of the circuit board 50, wherein an inwardly extending collar 58 is provided at the bottom face of the sleeve 56. A contact helical spring 60 is coaxially arranged in the sleeve 56, wherein the upper end of the contact helical spring 60 is connected to a contact terminal 68 of the circuit board. The lower end of the contact helical spring 60 is connected to a contact plate 62, the outer circumference of which abuts on the inner side of the collar 58 due to the pressure force of the contact helical spring 60. Furthermore, the sleeve 56 is surrounded by a second contact helical spring 64, the upper end of which is connected to a contact terminal 66 on the circuit board 50 and the lower end of which is arranged at the height of the collar 58 unless the second contact helical spring 64 is put under pressure.

The contact terminals 66, 68 are each conductively connected through the micro-switch 54 to the electronic circuit unit 52. The electronic circuit unit 52 is moreover connected through a positive line (not shown) to the LED 36, which is guided through a through-hole 34 in the basic body 12. The negative line of the LED 36 is electrically connected to the housing 90 of the battery grip 11.

FIG. 1 shows the use of a battery unit 71 as a voltage source for the illumination device 10, consisting of two dry batteries connected in series and arranged in the grip housing 90, wherein only the uppermost dry battery 70 is shown. The top side of the dry battery 70 abuts on the end face of the sleeve 56, wherein the central positive pole 72 extends through the opening in the collar 58 and abuts on the bottom side of the contact plate 62, so that the positive pole 72 is conductively connected to the electronic circuit unit 52. The negative pole is formed by the grip housing 90 of the battery grip 11.

FIG. 2 shows the use of an accumulator unit 74 arranged in the grip housing 90 as a voltage source instead of the battery unit 71. The end face of the cylindrical accumulator unit 74 has a central cylindrical recess 78, the diameter of which is larger than the outer diameter of the sleeve 56. The second contact helical spring 64 surrounding the sleeve 56 presses against the bottom of the recess 78, whereby a conductive connection of the positive pole of the accumulator unit 74 with the electronic circuit unit 52 is formed. The bottom of the recess 78 abuts on the face of the sleeve 56.

Figure 3:
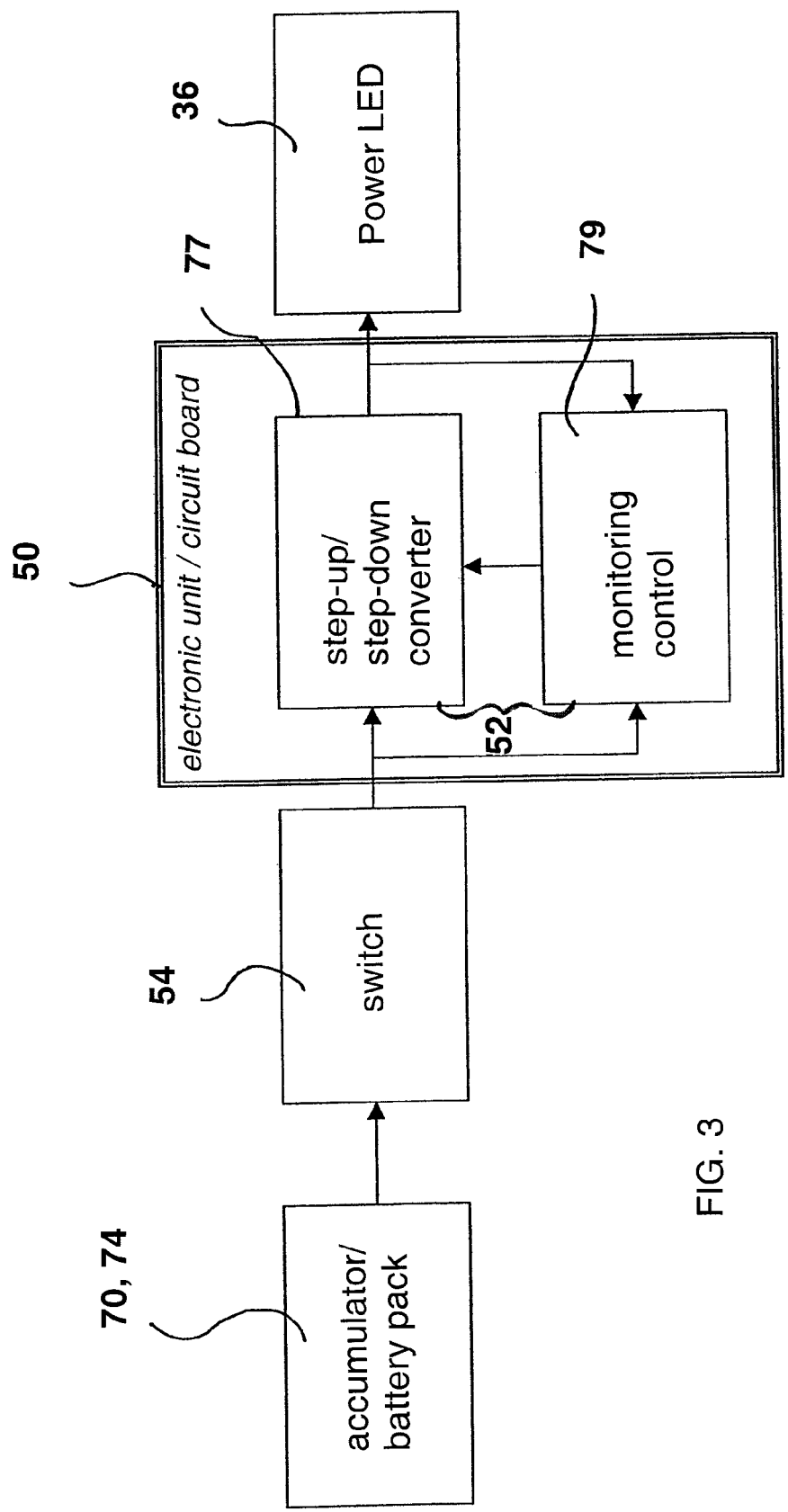
FIG. 3 is a block diagram of the illumination device of FIG. 1.

FIG. 3 shows a block diagram of the line connection between the accumulator/battery pack 70, 74 and the LED 36. A micro-switch 54 is arranged between the electronic circuit unit 52 on the circuit board 50, through which micro-switch 54 the conductive connection between accumulator/battery pack 70, 74 and the electronic circuit unit 52 can be interrupted and restored.

The electronic circuit unit 52 comprises a control and monitoring unit 79 as well as a step-up/step-down converter 77, which is controlled by the control and monitoring unit 79 and is able to apply power of two different levels to the LED 36, wherein the power of the lower level can, for example, amount to 100 mA and the power of the higher level can, for example, amount to 350 mA. In this case, the LED is operated constantly with a voltage of 3 V.

The electronic circuit unit 52 is configured and designed such that it is able to perform two operating modes, namely a first operating mode in case a battery unit 71 is used as a voltage source and a second operating mode in case an accumulator unit 74 is used as a voltage source. Herein the electronic circuit unit 52 is formed and configured such that it makes sure that a switch-off takes place as soon as the battery or accumulator voltage reaches a lower threshold, wherein in case the battery or accumulator voltage goes below this threshold, this would lead to damage of the battery unit or the accumulator. As long as the battery or the accumulator voltage does not go below an upper threshold, the LED is operated through the step-up/step-down converter 77 with the power of the higher level, so that it has a constant high brightness. If the voltage of the battery unit or the accumulator unit goes below the upper threshold, but is higher than the lower threshold, the control and monitoring unit 79 of the electronic circuit unit 52 delivers a corresponding signal to the step-up/step-down converter 77, whereupon the latter selects the lower power level for the LED 36, so that the LED illuminates with a smaller, but constant brightness until the voltage falls below the lower threshold. Then the illumination is turned off.

Figure 4:
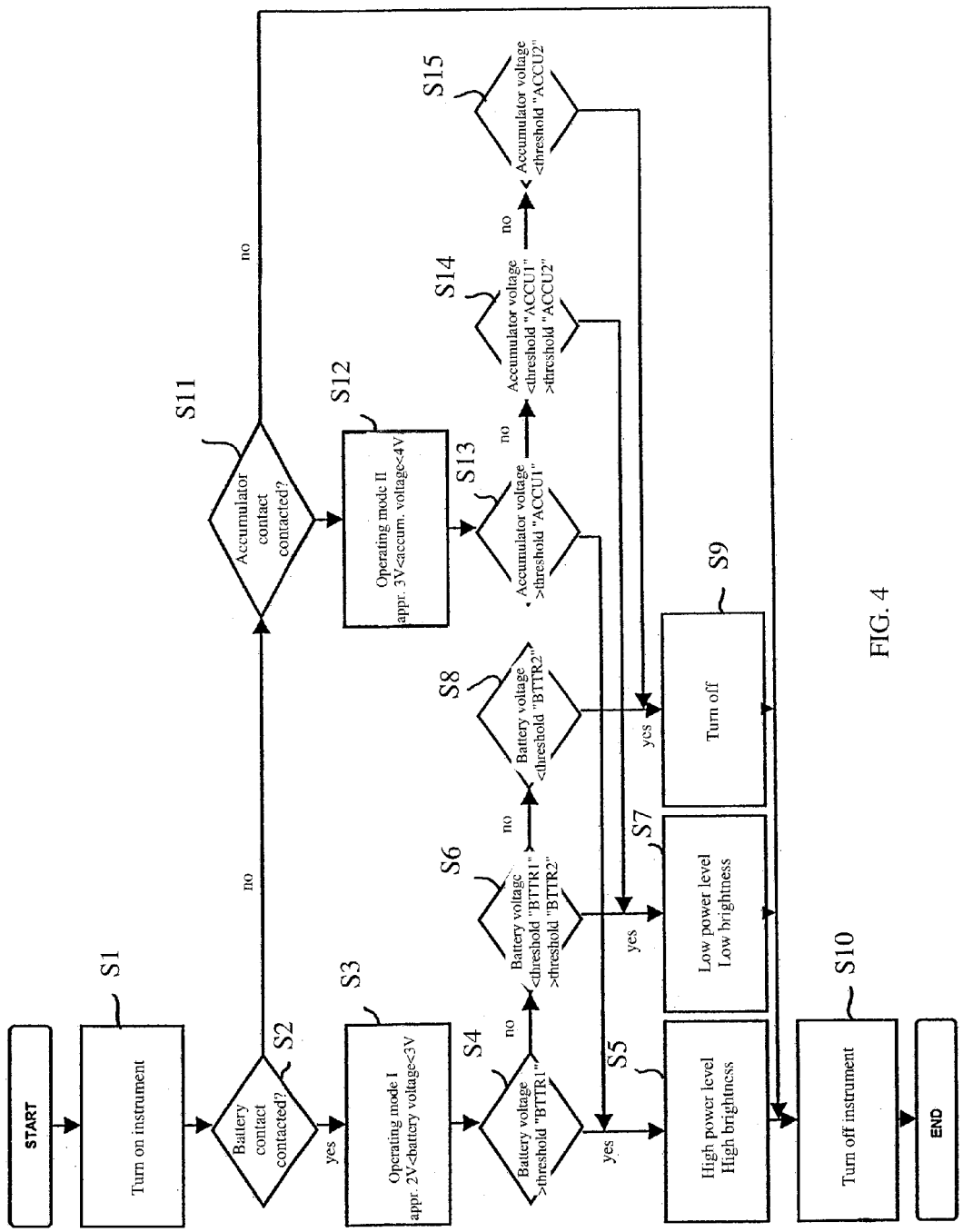
FIG. 4 is a flow chart for the control of the illumination device of FIG. 1 by means of a first electronic circuit unit.

A corresponding flow chart is shown in FIG. 4 and will be described hereinafter. At first the instrument is turned on by actuating the micro-switch 54 (step S1). Then the electronic circuit unit checks whether there is a voltage applied at the contact terminal 68. If yes, the electronic circuit unit 52 determines that the battery contact is contacted (step S2) and selects a first battery mode in which the battery voltage is to be between 2 V and 3 V (step S3). Thereafter it is determined whether the battery voltage exceeds a first threshold BTTR1 (step S4). If yes, the electronic circuit unit 52 selects a high power level through the step-up/step-down converter 77, so that a constant power of, for example, 350 mA is applied to the LED (step S5). If the electronic circuit unit 52 detects that the battery voltage is below the threshold BTTR1, but above a second threshold BTTR2 (step S6), the step-up/step-down converter 77 is controlled by the control and monitoring unit

79 such that it sets the lower power level in which the LED 36 is operated at a constant power of, for example, 100 mA (step S7).

If, however, it is detected that the battery voltage even goes below the second threshold BTTR2 (step S8), the current supply of the LED 36 is turned off (step S9).

If after the instrument has been turned on (step S1) it is detected in step S2 that the battery contact 68 is not contacted, the electronic circuit unit 52 checks whether the accumulator contact 66 is contacted (step S11). If this is the case, in step S12 a second operating mode is selected in which the allowed voltage range is between approx. 3 V and 4 V. Thereafter the electronic circuit unit checks whether the accumulator voltage is above a threshold ACCU1 (step S13). If yes, the operation proceeds to step S5, which means that the high power level is selected for the LED 36. If the accumulator voltage is between the upper threshold ACCU1 and a second lower threshold ACCU2 (step 14), step S7 is selected, which means that the lower power level is selected for the LED 36. If, however, the accumulator voltage even goes below the second threshold ACCU2, the LED 36 is turned off in step S9.

In the first and second operating modes the voltages are continuously checked until the instrument is turned off in step S10.

In the case of the embodiment described above the battery unit comprises two dry batteries having a nominal voltage of 1.5 V each, and the accumulator unit has a nominal voltage of 4 V. Depending on the operating voltage of the LED used, accumulator units or battery units having higher or lower nominal voltages can be used, too. In this case, the respective second thresholds have to be set such that damage of the accumulator units or battery units is avoided. Further, the second threshold must be adapted correspondingly and is preferably 0.4 V above the second threshold.

Figure 6:
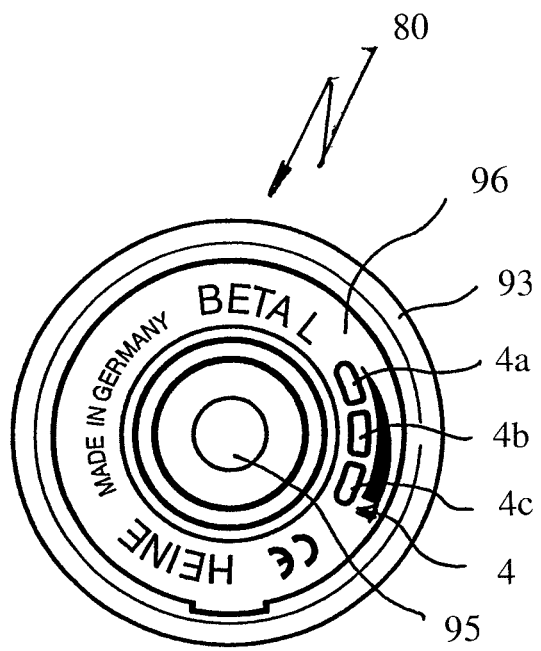
FIG. 6 is a bottom view of the bottom unit of FIG. 5.
Figure 5:
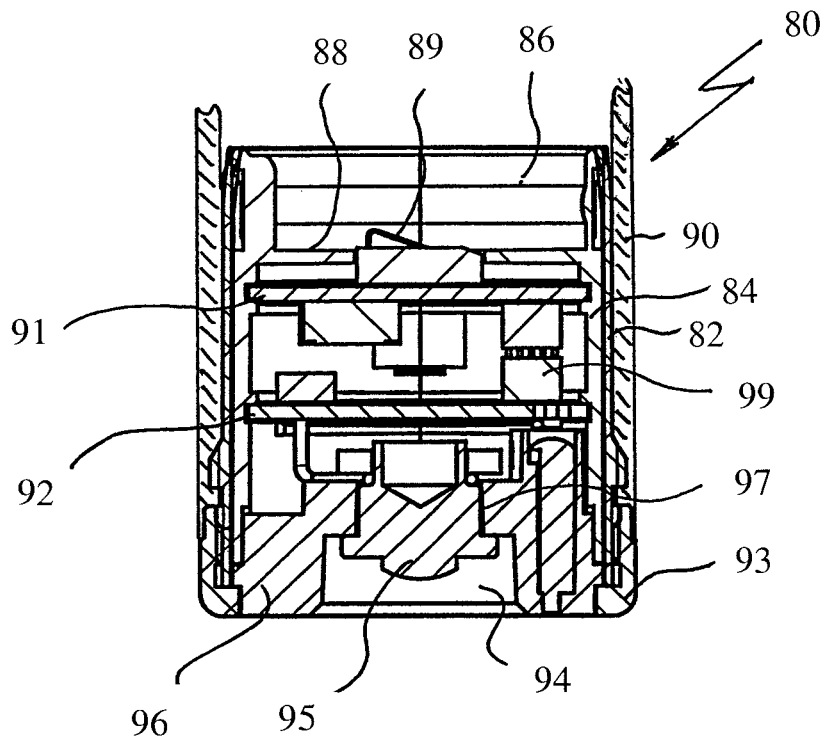
FIG. 5 is a longitudinal cross section of a bottom unit of the battery grip.

FIGS. 5 and 6 show a bottom unit 80 mounted at the lower end of the grip sleeve 90. The bottom unit 80 comprises a rotationally symmetrical basic body 84 made of plastics surrounded by a metal sleeve 84, the outer diameter of which substantially corresponds to the inner diameter of the grip sleeve 90 and is inserted into the lower end of the grip sleeve 90. A cavity 86 for receiving the lower end of an accumulator unit 74 (FIG. 2) is formed in the upper face of the basic body 84. The lower end of the basic body 84 is closed by a bottom piece 96 made of plastics, which is held by a metal ring 93 screwed onto the lower end of the metal sleeve 82, wherein the upper end face of the metal ring 93 abuts on the lower end of the grip sleeve 90, which is also formed of metal. Two circuit boards 91, 92 are spaced apart within the basic body 84 between the bottom 88 of the cavity 86 and the bottom piece 96 such that their plane extends perpendicularly to the middle axis of the basic body 84. An charging electronic circuit unit 99 is arranged on the circuit boards 91, 92, the design of which is explained in more detail hereinafter with respect to FIG. 7.

A contact element 89 extends from below through the bottom 88 of the cavity 86 and generates an electrical connection of the charging electronic circuit unit 99 to the positive pole of the accumulator unit 74. A through-hole 97 is formed centrally in the bottom piece 96 adjacent a cavity 94 in the lower face of the bottom piece 96. A contact element 95 is arranged in the through-hole 97, wherein the lower end of the contact element 95 ends in the cavity 94 and the upper end thereof is electrically connected to a positive conductor path of the circuit board 99. The negative contact is formed by the metal ring 93 and the metal sleeve 82.

Figure 7:
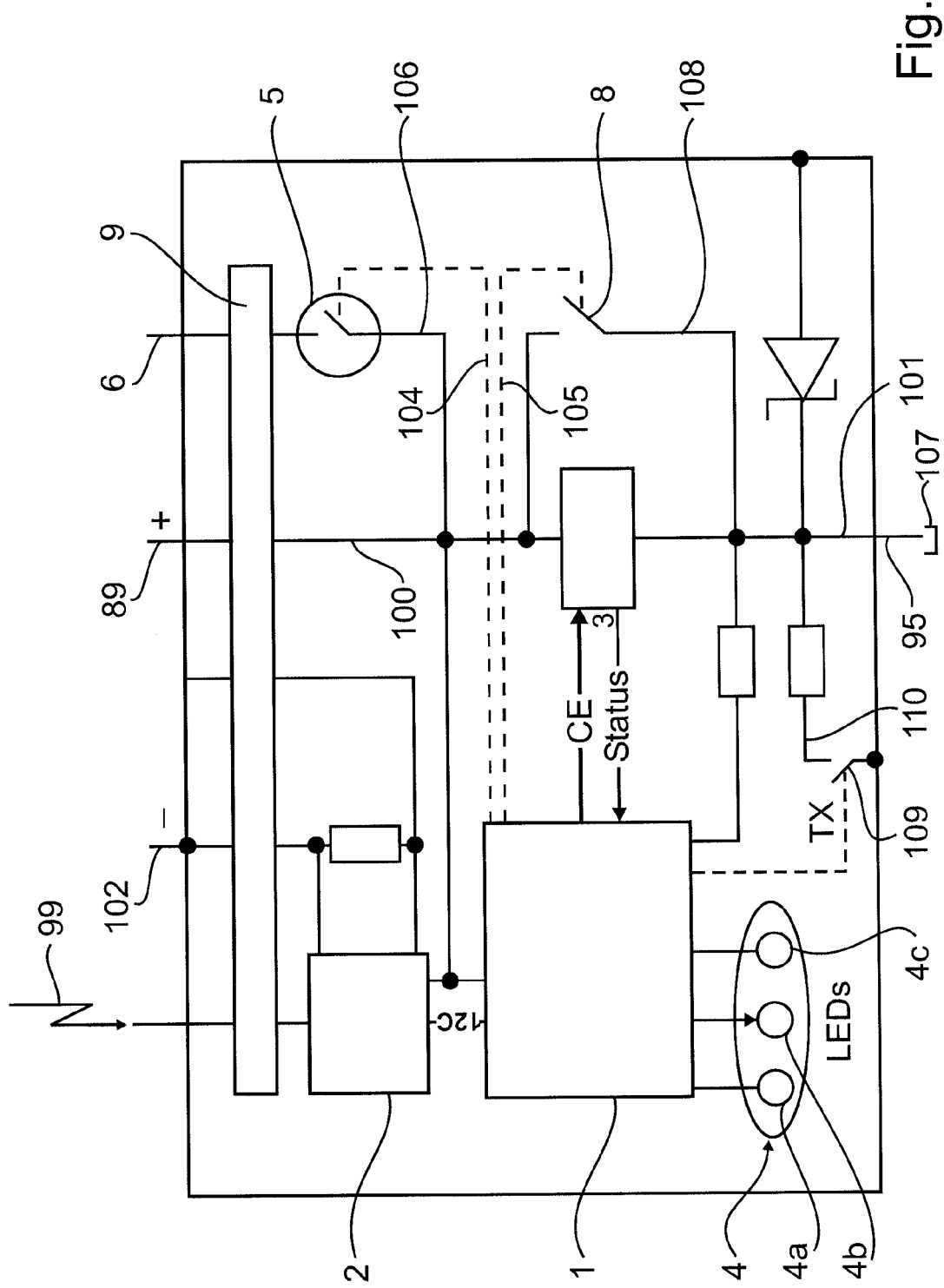
FIG. 7 schematically shows the basic structure of an charging electronic circuit unit for the bottom unit of FIG. 5.

FIG. 7 shows the basic structure of the charging electronic circuit unit 99. The charging electronic circuit unit 99 has a microprocessor 1 as the central element. Furthermore, a charging state measuring means 2 is provided which, on the one hand, is connected to a negative contact 102 and, on the other hand, through a conductor path 100 to the contact element 89, which contacts the positive pole of the accumulator unit 74. The charging state measuring means 2 detects the charging state of the accumulator unit 74 and delivers a corresponding signal to the microprocessor 1. Furthermore, an LED means 4 is provided having three LEDs 4a, 4b, 4c of different colors, which are activated by the microprocessor 1 corresponding to the respective charging state.

A table is stored in the microprocessor 1, from which the microprocessor 1 reads the respective optimal charging voltage for a certain measured charging state. The microprocessor 1 forwards this charging voltage to a charging regulator 3 connected through the conductor path 100 to the contact element 89. Another output of the charging regulator 3 is connected through a conductor path 101 to the contact element 95. Moreover, the conductor path 100 is connected through a conductor path 106 to a consumer load 6, for example, to the positive line of the illumination device 10, wherein a switch 5 is arranged in the conductor path 106, which switch 5 is controlled by the microprocessor 1 through a line 104.

The conductor path 100 and the conductor path 101 can be connected through a conductor path 108, which bypasses the charging regulator 3. A switch 8 is arranged in the conductor path 108, which switch 8 is also controlled by the microprocessor 1. If the switch 8 is closed, a direct connection is established between the conductor paths 100 and 101 and thus between the contact element 95 and the contact element 89. Eventually, an ESD element 9 is provided, which protects the elements of the charging electronic circuit unit 99 from electrostatic charge.

When the battery grip 11 is inserted into a charging station and a contact between a contact element 107 of the charging station applied with current and the contact element 95 is established, the microprocessor 1 exchanges a corresponding communication protocol through a line 110, in which a switch 109 is arranged, and thereafter establishes the connection between the charging station and the bottom unit 80. The charging state of the accumulator unit 74 is detected through the charging state measuring means 2 and forwarded to the microprocessor 1. By specifically detecting the momentary charging state through the charging state measuring means 2 the microprocessor 1 uses the stored table to determine the values for optimizing the charging time and controls the charging regulator 3 correspondingly. The associated different charging currents to the accumulator unit 74 through the contact element 89 are controlled by the charging regulator 3 and fed into the accumulator unit 74. Herein a differentiation is made between quick charging, charging and maintenance of charge.

If the exchange of the communication protocol between the microprocessor 1 and the charging station is not successful, the switch 8 is closed.

When the battery grip 11 is taken from the charging station again, the contact between the contact elements 95 and 107 is interrupted and the momentary charging state is indicated by means of one or more of the LEDs 4a, 4b, 4c of the LED means, wherein the LEDs 4a, 4b, 4c are correspondingly controlled by the microprocessor 1. Furthermore the microprocessor 1 controls the LED means 4 such that the LEDs 4a, 4b, 4c are turned off again after a predetermined period of time in order to spare energy of the accumulator unit 74.

The microprocessor 1 activates the charging state display 4 also in cases where the grip is not directly taken from the charging station, but in the state of being taken it is connected to the consumer load 6.

Depending on the consumer load 6 used it is possible that in case the consumer load is turned on more current is consumed than can be loaded. In order not to discharge the accumulator unit 74 any further although it should in fact be charged and in order to spare the lamp in, for example, the illumination means 10, the microprocessor 1 checks after the battery grip 11 has been inserted in the charging station whether the consumer load 6 is turned on or off. If the consumer load 6 is not turned off, the microprocessor activates the switch 5 such that the current supply of the consumer load 6 through the conductor path 106 is interrupted. If the battery grip is taken from the charging station again, the switch 5 is closed again, so that the consumer load 6 is supplied with current.

If in case a battery grip 11 has been inserted into a charging station the microprocessor 1 recognizes that a charge control is already provided in the charging station, the microprocessor 1 closes the switch 8 whereby a direct contact of the contact elements 89, 95 is established through the conductor paths 101, 108 and 100 and a charge control of the charging electronic circuit unit 99 is interrupted.

The invention claimed is:

1. An illumination device, particularly for medical diagnostic instruments, comprising at least one LED, which can be connected through circuit means to a voltage source selectively formed by a battery unit or an accumulator unit which are mutually interchangeable, wherein first contact means for connecting the battery unit to said circuit means and second contact means for connecting said accumulator unit to said circuit means are provided.

2. The illumination device according to claim 1, wherein said circuit means comprise an electronic circuit unit connected to said first contact means and to said second contact means as well as to said LED, wherein said electronic circuit unit is formed and configured such that it performs a first operating mode when said first contact means is connected to said battery unit, and performs a second operating mode when said second contact means are connected to said accumulator unit.

3. The illumination device according to claim 2, wherein said electronic circuit unit is formed and configured such that in said first operating mode
a first power is applied to said LED if a battery voltage exceeds a first battery threshold, and
no power is applied to said LED if said battery voltage falls below said first battery threshold by a certain extent.

4. The illumination device according to claim 3, wherein said first battery threshold amounts to 2.2 V to 2.6 V.

5. The illumination device according to claim 2, wherein said electronic circuit unit is formed and configured such that in said first operating mode
a first power is applied to said LED if a battery voltage exceeds a first battery threshold, and
a second power is applied which is lower than said first power to said LED if said battery voltage goes below said first battery threshold and is higher than a second battery threshold which is lower than said first battery threshold.

6. The illumination device according to claim 5, wherein said first battery threshold amounts to 2.2 V to 2.6 V and said second battery threshold amounts to 1.8 V to 2.2 V.

7. The illumination device according to claim 2, wherein said electronic circuit unit is formed and configured such that in said second operating mode
a first power is applied to said LED if said accumulator voltage exceeds a first accumulator threshold, and
no power is applied to said LED if said accumulator voltage goes below said first accumulator threshold by a certain extent.

8. The illumination device according to claim 7, wherein said first accumulator threshold amounts to 3.2 V to 3.6 V.

9. The illumination device according to claim 2, wherein said electronic circuit unit (52) is formed and configured such that in said second operating mode
a first power is applied to said LED if said accumulator voltage exceeds a first accumulator threshold, and
a second power is applied which is lower than said first power to said LED if said accumulator voltage goes below said first accumulator threshold and is higher than a second accumulator threshold which is lower than said first accumulator threshold.

10. The illumination device according to claim 9, wherein said first accumulator threshold amounts to 3.2 V to 3.6 V and said second accumulator threshold amounts to 2.8 V to 3.2 V.

11. The illumination device according to claim 2, wherein said first and said second contact means are connected through an ON/OFF switch (54) to said electronic circuit unit.

12. The illumination device according to claim 3, wherein said first power can be adjusted through a potentiometer.

13. A battery grip for medical diagnostic instruments including an illumination device comprising at least one LED, which can be connected through circuit means to a voltage source selectively formed by a battery unit or an accumulator unit which are mutually interchangeable, wherein first contact means for connecting the battery unit to said circuit means and second contact means for connecting said accumulator unit to said circuit means are provided.

14. The battery grip according to claim 13, further including a grip sleeve in which said accumulator unit can be arranged, and a bottom unit comprising a basic body mountable to a lower end of said grip sleeve, wherein an upper contact element for contacting said accumulator unit and a lower contact element for contacting a charging station contact element, to which a current is applied, are arranged in said basic body, wherein a charging electronic circuit unit having a microprocessor is connected between said upper and said lower contact elements, which charging electronic circuit unit is formed and configured such that it controls a charging process for charging said accumulator unit, wherein said charging electronic circuit unit comprises charging state measuring means configured such that it measures a momentary charging state of an accumulator unit and delivers a corresponding signal to said microprocessor, a table is stored in said microprocessor for optimizing a charging time depending on said momentary charging state of said accumulator unit, and said microprocessor is formed and configured such that it controls a charge regulator for regulating the charge of said accumulator unit corresponding to said table stored.

15. A bottom unit for a battery grip for medical diagnostic instruments, the battery grip comprising a grip sleeve in which an accumulator unit is arranged, which can be connected to a consumer load of an illumination device, the bottom unit comprising a basic body mountable to a lower end of said grip sleeve, wherein an upper contact element for contacting said accumulator unit and a lower contact element for contacting a charging station contact element, to which a current is applied, are arranged in said basic body, wherein a charging electronic circuit unit having a microprocessor is connected between said upper and said lower contact elements, which charging electronic circuit unit is formed and configured such that it controls a charging process for charging said accumulator unit.

16. The bottom unit according to claim 15, wherein
said charging electronic circuit unit comprises charging state measuring means configured such that it measures a momentary charging state of an accumulator unit and delivers a corresponding signal to said microprocessor,
a table is stored in said microprocessor for optimizing a charging time depending on said momentary charging state of said accumulator unit, and
said microprocessor is formed and configured such that it controls a charge regulator for regulating the charge of said accumulator unit corresponding to said table stored.

17. The bottom unit according to claim 15, wherein a charging state display comprising one or more LEDs is provided at a bottom side of said bottom unit and said charging electronic circuit unit is formed and configured such that it displays a charging state of said accumulator unit through said charging state display.

18. The bottom unit according to claim 17, wherein said charging electronic circuit unit is formed and configured such that it turns off said charging state display when said lower contact element comes into contact with said charging station contact element.

19. The bottom unit according to claim 17, wherein said charging electronic circuit unit is formed and configured such that it turns on said charging state display if said contact of said lower contact element with said charging station contact element is interrupted.

20. The bottom unit according to claim 19, wherein said charging electronic circuit unit is formed and configured such that it turns off said charging state display again after a predetermined period of time has expired after it has been turned on.

21. The bottom unit according to claim 16, wherein said charging electronic circuit unit comprises a switch in a conductor path connectable to a consumer load, and said microprocessor is formed and configured such that it opens said switch when said lower contact element comes into contact with said charging station contact element.

22. The bottom unit according to claim 21, wherein said microprocessor is formed and configured such that it closes said switch if said contact between said lower contact element and said charging station contact element is interrupted.

23. A battery grip for medical diagnostic instruments, the battery grip comprising a grip sleeve in which an accumulator unit is arranged, which can be connected to a consumer load of an illumination device, and a bottom unit comprising a basic body mountable to a lower end of said grip sleeve, wherein an upper contact element for contacting said accumulator unit and a lower contact element for contacting a charging station contact element, to which a current is applied, are arranged in said basic body, wherein a charging electronic circuit unit having a microprocessor is connected between said upper and said lower contact elements, which charging electronic circuit unit is formed and configured such that it controls a charging process for charging said accumulator unit, wherein said charging electronic circuit unit comprises charging state measuring means configured such that it measures a momentary charging state of an accumulator unit and delivers a corresponding signal to said microprocessor, a table is stored in said microprocessor for optimizing a charging time depending on said momentary charging state of said accumulator unit, and said microprocessor is formed and configured such that it controls a charge regulator for regulating the charge of said accumulator unit corresponding to said table stored.

24. The battery grip according to claim 23, further including an illumination device comprising at least one LED, which can be connected through circuit means to a voltage source selectively formed by a battery unit or an accumulator unit which are mutually interchangeable, wherein first contact means for connecting the battery unit to said circuit means and second contact means for connecting said accumulator unit to said circuit means are provided, wherein said circuit means comprise an first electronic circuit unit connected to said first contact means and to said second contact means as well as to said LED, wherein said electronic circuit unit is formed and configured such that it performs a first operating mode when said first contact means is connected to said battery unit, and performs a second operating mode when said second contact means are connected to said accumulator unit.

* * * * *